United States Patent [19]

Ito et al.

[11] Patent Number: 5,112,615

[45] Date of Patent: May 12, 1992

[54] SOLUBLE HIRUDIN CONJUGATES

[75] Inventors: Ralph K. Ito, Quincy; Frank W. LoGerfo, Belmont, both of Mass.

[73] Assignee: New England Deaconess Hospital Corporation, Boston, Mass.

[21] Appl. No.: 592,554

[22] Filed: Oct. 4, 1990

Related U.S. Application Data

[63] Continuation-in-part of Ser. No. 227,700, Aug. 3, 1988.

[51] Int. Cl.⁵ .......................... A61F 2/00; A61K 31/00; C07K 3/00
[52] U.S. Cl. ................................ 424/426; 420/422; 514/2; 514/8; 523/112; 523/113; 530/300; 530/382; 530/395; 530/402; 530/810; 530/812; 530/813
[58] Field of Search ............... 424/422, 423, 426, 443; 523/112, 113; 604/266; 514/2, 8; 530/300, 382, 395, 402, 810, 812, 813, 816

[56] References Cited

U.S. PATENT DOCUMENTS

| | | | |
|---|---|---|---|
| 3,432,596 | 3/1969 | Markwardt et al. | 424/95 |
| 4,116,898 | 9/1978 | Dudley et al. | 260/17.4 |
| 4,378,803 | 4/1983 | Takagi et al. | 604/280 |
| 4,447,562 | 5/1984 | Ivani | 523/105 |
| 4,521,564 | 6/1985 | Solomon et al. | 525/54.1 |
| 4,563,485 | 1/1986 | Fox, Jr. et al. | 523/113 |
| 4,594,407 | 6/1986 | Nyilas et al. | 528/272 |
| 4,600,652 | 7/1986 | Solomon et al. | 428/423.3 |
| 4,654,302 | 3/1987 | Fritz et al. | 435/70 |
| 4,668,662 | 5/1987 | Tripier | 514/12 |
| 4,680,177 | 7/1987 | Gray et al. | 424/101 |
| 4,713,448 | 12/1987 | DeVore et al. | 530/356 |
| 4,720,512 | 1/1988 | Hu et al. | 523/112 |
| 4,734,097 | 3/1988 | Tanabe et al. | 623/11 |

FOREIGN PATENT DOCUMENTS

| | | |
|---|---|---|
| 0168342 | 1/1986 | European Pat. Off. |
| 0171024 | 2/1986 | European Pat. Off. |
| 0193175 | 9/1986 | European Pat. Off. |
| 0207956 | 1/1987 | European Pat. Off. |
| 0225633 | 6/1987 | European Pat. Off. |
| 0252854 | 1/1988 | European Pat. Off. |
| WO79/00638 | 9/1979 | PCT Int'l Appl. |
| WO86/03517 | 6/1986 | PCT Int'l Appl. |
| 2164343 | 3/1986 | United Kingdom |

OTHER PUBLICATIONS

Lyman et al. (1965) Trans. Amer. Soc. Artif. Int. Organs XI:301-306.
Markwardt (1970), Methods in Enzymology 19:924-932.
Falb et al. (1971) Federation Proceedings 30:1688-1691, No. 5.
Kusserow et al. (1971) Trans. Amer. Soc. Artif. Organs XVII:1-5.
Salyer et al. (1971) J. Biomed. Mater. Res. Symposium 1:105-127.
Badgy et al. (1976) Methods in Enzymology 45:669-678.
Lindon et al. (1978) J. Lab. Clin. Med. 91:47-59.
Salzman et al. (1980) J. Clin. Investigation 65:64-73.
Van Obberghen-Schilling et al. Biochem. and Biophys. Res. Comm. 106:79-86.
Merrill et al. (1983) ASAIO Journal 6:60-64, No. 2.
Hoffmann et al. (1984) Haemostasis 14:164-169.
Bizios et al. (1985) Thrombosis Research 38:425-431.
Lindon et al. (1985) J. Lab. Clin. Med. 105:219-226, No. 2.

(List continued on next page.)

Primary Examiner—Thurman K. Page
Assistant Examiner—G. S. Kishore
Attorney, Agent, or Firm—Lahive & Cockfield

[57] ABSTRACT

Disclosed is a soluble, biocompatible, pharmacological agent for inhibiting thrombin generation and thrombus formation, and methods for producing the same. The pharmacological agent or conjugate includes a soluble, biocompatible carrier and a thrombogenesis inhibitor immobilized thereto via the carrier which binds the inhibitor. The thrombogenesis inhibitor is hirudin, or an active analog or active fragment thereof. The thrombogenesis inhibitor may be bound to the carrier via a bifunctional cross-linking reagent.

18 Claims, 5 Drawing Sheets

OTHER PUBLICATIONS

Kottke-Marchant et al. (1985) Dept. Pathol. Case W. R. Univ., pp. 842–848.
Castellot, Jr. et al. (1986) J. Cellular Physiology 127:323–329.
"Company Profile", Chemist & Druggist, Oct. 11 (1986).
Lane et al. (1986) J. Biological Chemistry 261:3980–3986, No. 9.
Clagett (1987) Hemostasis and Thrombosis 190:1348–1365, No. 1.
Clark et al. (1987) "Medicine", Newsweek Feb. 2.
Kriautiunas et al. (1987) Diabetes 36:163–168.
Krstenansky et al. (1987) J. Biochemistry 211:10–16, No. 1.
"Leeches U.S.A. Ltd." (1987) Medicinal Leeches.
Markwardt (1987) Instittue of Pharm. and Toxicol., p. 22.
Salzman et al. (1987) Hemostasis and Thrombosis, pp. 1335–1347.
Fareed et al. (1988) Loyola Univ. Medical Center Symposium.
Fenton (1988) Loyola University Medical Center Symposium.
Fink (1988) Loyola University Medical Center Symposium.
Ito et al. (1988) Abtracts 61st Scien. Sessions, Part II Circulation 78:324.
Krstenansky et al. (1988) B.B.A. 957:53–59.
Krstenansky et al. (1988) Thrombosis Research 52:137–141.
Messmore (1988) Loyola University Medical Center Symposium.
Sawyer (1988) Loyola University Medical Center Symposium.
Talbot et al. (1988) Loyola University Medical Center Symposium.
Walenga et al. (1988) Loyola University Medical Center Symposium.
Maraganore et al. (1989) J. Bio. Chem. 264:8692–8698, No. 15.
Wallace et al., (1989) Biochemistry, 28:10079–10084.
Tay et al. (1989) Biomateraisl 10:11–16.
Chang et al. (1990) FEBS Letters 260:209–212, No. 2.
Dodt et al., (1990) J. Bio. Chem. 265:713–718, No. 2.
Jakubowski et al. (1990) Blood 75:399–406, No. 2.
Krstenansky et al. (1990) Thrombosis and Haemostasis 63:208–214, No. 2.
Biopharm (UK) Limited.

```
                                                                10  (A)
H--Val----Val----Tyr---Thr---Asp---Cys----Thr---Glu---Ser---Gly--
                                                                20
--Gln---Asn----Leu---Cys---Leu---Cys----Glu---Gly---Ser---Asn--
                                                                30
--Val---Cys---Gly---Gln----Gly----Asn---Lys---Cys---Ile---Leu--
                                                                40
--Gly----Ser----Asp---Gly---Glu---Lys---Asn---Gln---Cys---Val--
                                                                50
--Thr---Gly---Glu---Gly---Thr---Pro---Lys---Pro---Gln---Ser--
                                                                60
--His---Asn---Asp---Gly---Asp---Phe---Glu---Glu---Ile---Pro--
                                         SO₃H
                                          |
                    ---Glu---Glu---Tyr---Leu---Gln---OH--
```

SOLUBLE HIRUDIN CONJUGATES

CROSS-REFERENCE TO RELATED APPLICATION

This application is a continuation-in-part of applicants' copending application Ser. No. 227,700, entitled "HIRUDIN-COATED BIOCOMPATIBLE SUBSTANCE", filed Aug. 3, 1988.

BACKGROUND OF THE INVENTION

The technical field of the present invention is thrombogenesis inhibitors, and more specifically involves soluble, pharmacologic agents useful for inhibiting thrombin generation and thrombin-mediated aggregation, and methods of their preparation and use.

Exposure of blood to artificial surfaces usually leads to deposition of a layer of adherent platelets, accompanied by activation of the intrinsic coagulation system, and ultimately to the formation of a thrombus. In fact, significant blood/materials interaction can occur on a single pass through a prosthetic arterial graft. The types of blood proteins initially adsorbed or bound to synthetic surfaces may include proteins involved in contact coagulation. Contact coagulation or the extrinsic pathway of coagulation is a complex pathway of biochemical events that induces fibrin formation, platelet and complement activation, chemotaxis, kinin generation, and activation of fibrinolytic components. In addition, each of these events augments subsequent biochemical pathways often controlled by positive and negative feedback loops. Thus, thrombosis induced by contact with artificial materials is a major obstacle in the development and use of internal prostheses and extracorporeal devices such as artificial vessels and organs, and cardiopulmonary bypass and hemodialysis equipment.

Materials having varying degrees of thromboresistance have been utilized in vascular prostheses with limited success. These materials include corroding (self-cleaning) metals, synthetic polymers such as polydimethyl siloxane, Teflon, acrylates and methacrylates such as polyethylene terphthalate, electrets, anionic copolymers, and hydrogels (for a review see Salzman et al. (1987) in *Hemostasis and Thrombosis, Basic Principles and Clinical Practice* (Colman et al., eds.) J. B. Lippincott Co., Phila. PA, pp. 1335-1347).

To decrease the chances of thrombosis due to extended periods of contact with such artificial materials, patients have been treated with systemically administered anti-coagulant, anti-platelet, and thrombolytic drugs. These include any compound which selectively inhibits thromboxane synthetase without affecting prostacycline synthetase, affects platelet adherence as well as aggregation and release, enhances vascular PGI2 production, and/or inhibits both thrombin- and thromboxane-mediated platelet aggregation. Such compounds include aspirin, sulfinpyrazone, dipyridamole, ticlopidine, and suloctidil. However, treatment with these drugs often elicits unwanted side effects including systemic hemorrhaging and the inability to initiate and complete desired clotting elsewhere in the body.

To improve on the thromboresistance of artificial materials, biologically active molecules having thrombolytic, anticoagulating, thrombogenesis-inhibiting, and/or platelet inhibiting abilities have been linked thereto. For example, heparin has been bound to artificial surfaces to reduce coagulation by activating various inhibitors of the intrinsic clotting system (Salzman et al. (1987) in *Hemostasis and Thrombosis: Basic Principles and Clinical Practice,* 2nd Ed., (Colman et al., eds.), Lippincott Co., Phila., PA, pp. 1335-1347). However, heparin enhances platelet responses to stimuli such as ADP or collagen, and promotes two adverse primary blood responses towards synthetic surfaces: platelet adhesion and aggregation. In addition, although surface-bound heparin/antithrombin complex may be passive towards platelets, the wide variety of effects it has on interactions with endothelial cell growth factor, inhibition of smooth muscle Proliferation, and activation of lipoprotein lipase raises questions as to what adverse effects it may induce over time.

Anti-platelet agents such as $PGE_1$, $PGI_2$ (experimental use only), cyclic AMP, and aspirin have also been attached to solid polymer surfaces These agents discourage the release of platelet factors that stimulate adverse healing responses in the vicinity of a vascular graft. They may also reduce platelet-aided thrombus formation by inhibiting platelet adhesion.

The exposure of many artificial surfaces to albumin prior to vascular contact results in reduced reactivity with platelets (NIH Publication No. 85-2185, September, 1985, pp. 19-63). Therefore, albumin has been used to coat extracorporeal surfaces before cardiopulmonary by-pass surgery. However, long-term thromboresistance has not been achieved by this procedure.

Fibrinolytically active streptokinase and urokinase, alone or in combination with heparin have been attached to artificial surfaces by Kusserow et al (Trans. Am. Soc. Artif. Intern. Organs (1971) 17:1). These enzymes reduce excessive fibrin deposition and/or thrombotic occlusions. However, the long term assessment of their ability to confer thromboresistance to a synthetic surface has not been determined.

Surface active agents such as Pluronic F-68 have also been immobilized on artificial surfaces, but do not appear to offer long term blood compatibility (Salyer et al. (1971) *Medical Applications of Plastics.* Biomed. Materials Res. Sym. (Gregor, ed.) No. 1 pp. 105).

Therefore, what is needed are better biocompatible materials which are thromboresistant in the long term and whose active components do not cause detrimental side affects.

An object of the present invention is to provide a synthetic, biocompatible, thromboresistant material useful for implantable and extracorporeal devices in contact with bodily fluids.

Another object is to provide an immobilized thrombogenesis inhibitor which is biologically active, and a method of preparing the same.

Yet another object is to provide a soluble, stabilized thrombogenesis inhibitor.

Still another object of this invention is to provide a method of inhibiting platelet aggregation, the release of platelet factors, and thrombogenesis at the localized site of the graft or prosthesis-blood interface, thus avoiding the systemic effect of antiplatelet and antithrombosis drugs.

SUMMARY OF THE INVENTION

Materials and methods are disclosed herein for the provision of biocompatible, thromboresistant substances useful as a component of implantable or extracorporeal devices in contact with the blood. Also disclosed are soluble, biocompatible pharmacologic agents which inhibit excessive thrombin generation and thrombus formation.

It has been discovered that a synthetic, biocompatible material can be made into a thromboresistant substance by immobilizing to it, by way of a base coat layer, the thrombogenesis inhibitor hirudin, or an active analog or active fragment thereof, in such a way that does not compromise the inhibitor's thrombogenesis inhibiting activity.

It has also been discovered that the base coat material can act as a soluble, biocompatible carrier of the thrombogenesis inhibitor to which it is immobilized. This thrombogenesis inhibitor/carrier conjugate is useful as a pharmacologic agent having an increased half-life and ability to maintain its activity in the vascular compartment relative to hirudin. This is important as hirudin is known to rapidly diffuse into extravascular spaces, and as the conjugate has the potential to maintain anticoagulant effects in the vascular compartment.

The term "thrombogenesis inhibitor" is used herein to describe a native protein, synthetic, or recombinant analogs of that protein, or fragments of the protein or analogs, all of which having the biological anti-thrombogenic activities of hirudin.

Synthetic materials contemplated by the instant invention are preferably polymers such as polyethylene terphthalate, nylon, polyurethane, cross-linked collagen, polytetrafluoroethylene, polyglycolic acid, and mixtures thereof, the most preferred polymeric material being polyethylene terphthalate. Other synthetic materials might also be used.

At least one layer of biocompatible base coat layers is adhered to at least one surface of the synthetic material. This base coat layer or carrier contains a component which binds the thrombogenesis inhibitor. Examples of such base coat or carrier components include proteins, polypeptides, peptides, lipoproteins, glycoproteins, glycosaminoglycans, hydrogels, synthetic polymers, and mixtures thereof.

In one preferred aspect of the invention, the base coat layer or carrier includes a polypeptide component such as serum albumin, fibronectin, or active analogs or active fragments thereof, from human, bovine, bacterial, or other sources, for example. In another aspect of the invention, the carrier is a second proteinous thrombogenesis inhibitor such as tissue plasminogen activator, streptokinase or urokinase, or active fragments, or active analogs thereof. Other materials might also be used to form the base coat layer or carrier.

In accordance with one aspect of the invention, the thrombogenesis inhibitor is immobilized on the synthetic material via a base coat layer which is adhered to least one surface of the synthetic material The base coat layer contains a component capable of binding the thrombogenesis inhibitor without compromising the biological activity of the inhibitor.

In exemplary aspects of the invention, the synthetic material is activated prior to having the base coat layer adhered thereto so as to enhances its ability to bind the base coat base layer. For example, in one preferred aspect, the synthetic material is contacted with a solution which makes available at least one chemically active group (e.g., a carboxylic acid group) in the material for binding to a bifunctional cross-linking reagent (e.g., carbodiimide). The material so treated is then put into contact with a solution containing the cross-linking carbodiimide reagent for a time sufficient to allow the chemically active group to bind thereto.

In another embodiment, the synthetic material may be contacted with a solution which removes impurities therein and/or thereon prior to the activation step described above.

The immobilization step may be carried out by initially contacting the thrombogenesis inhibitor with at least one molecule of a bifunctional cross-linking reagent for a time sufficient to allow linkage of the reagent to the inhibitor, and then binding the thrombogenesis inhibitor-linked reagent to the base coat layer or carrier. The bound thrombogenesis inhibitor retains its thrombogenesis inhibiting activity A bifunctional cross-linking reagent useful for such an immobilization step may be heterobifunctional (e.g., N-succinimidyl 3-(2-pyridyldithio)propionate (SPDP)), homobifunctional (e.g., ethylene glycolbis (succinimidylsuccinate), (EGS)), or a mixture of both.

The term "bifunctional cross-linking reagent" is defined herein as a molecule having the ability to bind to, and therefore link, two reactive groups on, for example, one molecule or two separate molecules. If the bifunctional cross-linking reagent binds two different types of groups, it is a "heterobifunctional" cross-linking reagent. However, if the bifunctional cross-linking reagent binds only to two similar groups, it is "homobifunctional".

Prior to the binding step, the thrombogenesis-linked reagent may be subjected to chromatographic procedures to remove impurities mixed in with it.

In an alternative aspect of the invention, the base coat adhered to the synthetic material may be linked at the same time to at least one molecule of a bifunctional cross-linking reagent. In this embodiment, the method further includes binding the thrombogenesis inhibitor-linked reagent to the base coat-linked reagent, thereby linking the thrombogenesis inhibitor to the material-adhered base coat layer.

In yet another aspect of the invention, the base coat is linked to the thrombogenesis inhibitor before it is linked to the synthetic, biocompatible material.

The soluble pharmacologic agent or conjugate is produced by immobilizing the thrombogenesis inhibitor to a carrier. In preferred aspects of the invention immobilization includes contacting the inhibitor with at least one molecule of a bifunctional cross-linking reagent for a time sufficient to allow linkage of the reagent to the inhibitor. The carrier is then bound to the inhibitor-linked reagent. Alternatively, or in addition, the carrier is contacted with a cross-linking reagent and then is bound via the reagent to the inhibitor or to a reagent-linked inhibitor.

In another aspect of the invention, the base coat-linked or carrier-linked reagent is reduced prior to the binding step. The resulting exposed sulfhydryl group is then contacted with the inhibitor-linked reagent. Reduction results in the formation of sulfhydryl groups on the base coat or carrier which can react with the inhibitor-linked, bifunctional cross-linking reagent via a substitution reaction to form a disulfide bond, thereby covalently linking the thrombogenesis inhibitor to the base coat layer or carrier.

The invention will next be described in connection with certain illustrated embodiments. However, it should be clear that various modifications, additions, and deletions can be made without departing from the spirit or scope of the invention.

BRIEF DESCRIPTION OF THE DRAWING

The foregoing and other objects of the Present invention, the various features thereof, as well as the inventions thereof may be more fully understood from the following description when read together with the accompanying drawings in which.

DESCRIPTION OF THE INVENTION

Figure 1:
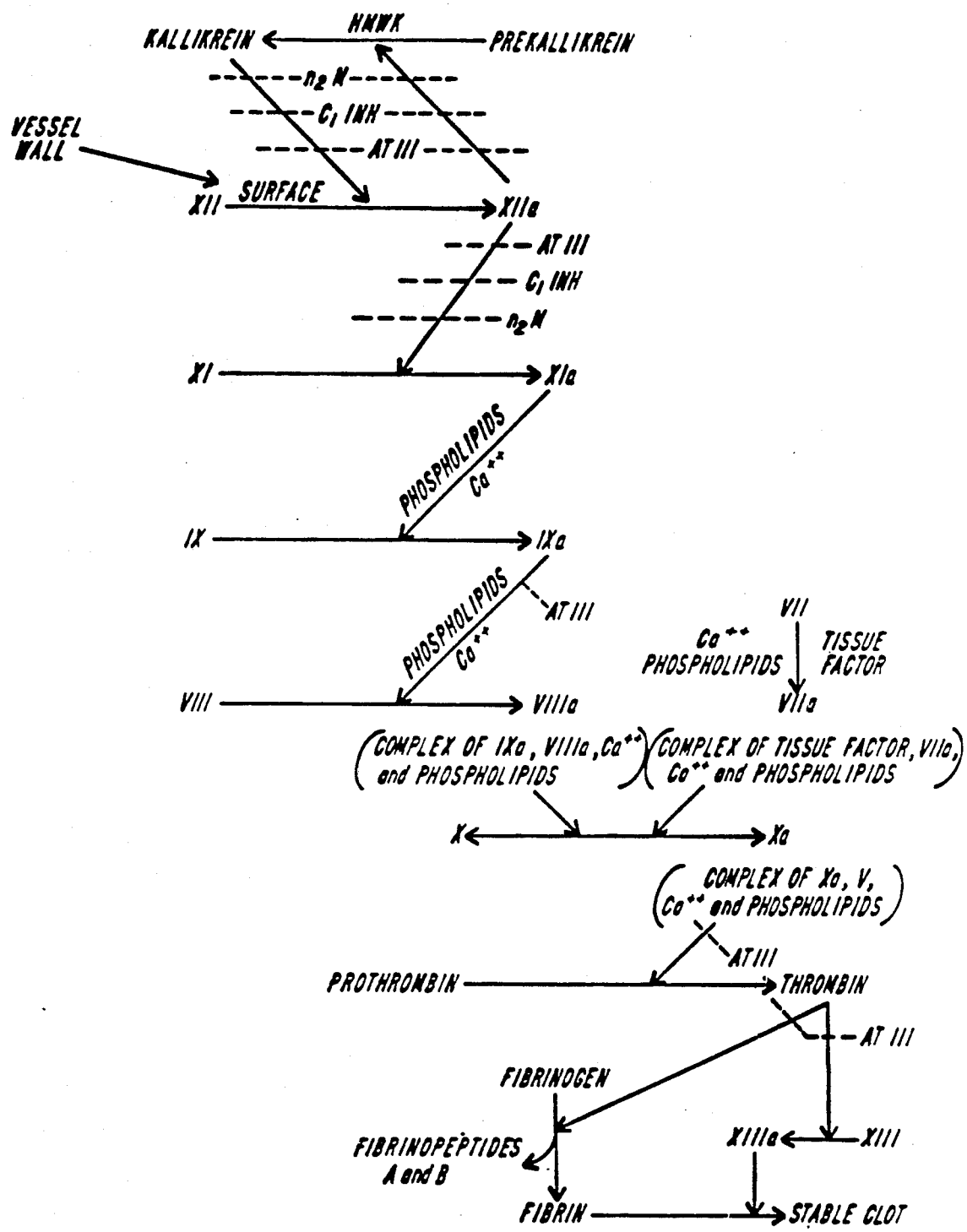
FIG. 1 is a diagrammatic representation of the pathways involved in thrombogenesis.

This invention provides biocompatible, thromboresistant substances useful for implantable and extracorporeal devices in contact with the vascular system, and methods for their fabrication.

The substances provided by this invention include a synthetic biocompatible substance having a thrombogenesis-inhibiting reagent linked thereto via a biocompatible base coat adhered to the material's surface.

The material useful in a prosthetic extracorporeal or implantable device may be composed of any biocompatible, synthetic, preferably polymeric material having enough tensile strength to withstand the rigors of blood circulation, and having groups onto which a base coat can be directly or indirectly bound. Examples of such synthetic materials are polytetrafluoroethylene (Teflon) and polyethylene terphthalate, nylon, and the like. The material may have any dimensions suitable for the purpose for which it is being used. For example, it may be an integral part of an implanted heart valve or of an extracorporeal device used for hemodialysis or cardiopulmonary by-pass surgery, or it may be used to coat catheters or to line the interior of a vascular graft.

The synthetic material, when obtained, may be coated with or contain various noncovalently adhered impurities whose removal may be prerequisite for the adherence of a base coat thereto. For example, lubricants on commercial quality polyethylene terphthalate can be removed by contacting the polyethylene terphthalate with a solution containing, for example, various detergents, solvents, or salts, which loosen and/or solubilize these impurities.

TABLES 1 and 2 outline representative methods of preparing the biocompatible, thromboresistant substance, where "Da" refers to a synthetic material composed of woven polyethylene terphthalate fibers, and "HSA" refers to human serum albumin, "EDC" refers pyridine-2-thione.

TABLE 1

| STEP # | PROCESS |
|---|---|
| 1) | Da + NaOH → Da—COOH |
| 2) | Da—COOH + EDC → Da—EDC |
| 3) | Da—EDC + HSA → Da—HSA + urea (EDC by-product) |
| 4) | Da—HSA + SPDP → Da—HSA—SPDP |
| 5) | Da—HSA—SPDP + DTT → Da—HSA—SH + P-2-T |

TABLE 1-continued

| STEP # | PROCESS |
|---|---|
| 6) | Inhibitor + SPDP → Inhibitor-SPDP |
| 7) | Da—HSA—SH + Inhibitor-SPDP → Da—HSA—S—S-Inhibitor + P-2-T |

TABLE 2

| STEP # | PROCESS |
|---|---|
| 1) | HSA + SPDP → HSA—SPDP |
| 2) | HSA—SPDP + DTT → HSA—SH + P-2-T |
| 3) | Inhibitor + SPDP → Inhibitor-SPDP |
| 4) | HSA—SH + Inhibitor-SPDP → HSA—S—S-Inhibitor + P-2-T |
| 5) | Da + NaOH → Da—COOH |
| 6) | Da—COOH + EDC → Da—EDC |
| 7) | Da—EDC + HSA—S—S-Inhibitor → Da—HSA—S—S-Inhibitor + urea (EDC by-product) |

Initially, the material may be activated so as to enhance the binding of the base coat layer. This activating step increases the number of chemically active groups int he material. For example, alkaline hydrolysis may be performed to increase the number of reactive carboxylic acid groups in the polyethylene terphthalate to which a bifunctional cross-linking reagent such as carbodiimide may be bound. Ultimately, the base coat will adhere to the bound carbodiimide groups on the material. However, this method must be performed with care, as alkaline hydrolysis partially degrades the polyethylene terphthalate, resulting in a fraying of the material's fibers.

At least one base coat layer is adhered to at least one surface of the synthetic material.

This layer, either adhered to the material or unbound, provides components for attachment of the thrombogenesis inhibitor. Such components provide more binding sites for the inhibitor than the synthetic material, alone, thereby amplifying the amount of inhibitor which may be bound. Useful components include proteins, peptides, lipoproteins, glycoproteins, glycosaminoglycans, synthetic polymers, and mixtures thereof. Proteins such as serum albumin and fibronectin are particularly useful for this purpose as they are known to have antithrombogenic properties, themselves, are very desirable as base coat components (Lyman et al. (1965) Trans. Am. Soc. Artif. Intern. Organs 11:301; Falb et al. (1971) Fed. Proc. 30:1688). An HSA molecule, for example, has 65 amino groups available as binding sites.

Attachment of the base coat to the artificial surface may be covalent in nature. Methods to covalently bind proteins to polyethylene terphthalate involve attack of the free reactive succinimide ester group of the cross-linking reagent to primary amino groups on a protein. As shown in the example in TABLE 1, to covalently adhere the base coat to polyethylene terphthalate, the polyethylene terphthalate is initially treated with 0.5 N NaOH and reacted with carbodiimide before it is coated with HSA (base coat) in phosphate buffered saline (PBS).

A thrombogenesis inhibitor useful as a coating for surfaces in contact with blood, bodily fluids, or tissues, is then covalently adhered to the base coat via the component. Inhibitor-coated substances are ideal for implantable use in devices which are in direct contact with blood. For example, by-pass grafts used to replace blood vessels often become filled with blood clots or thrombi, resulting in restricted blood flow. Since the inhibitor-coated substance is resistant to formation of blood clots, thrombosis and subsequent blockage of the bypass graft will be prevented. Likewise when catheters are placed into the vascular system for a diagnostic or therapeutic purposes, a blood clot often forms on the outside of the catheter. The clot may be washed off the catheter by flowing blood, or be jarred loose by manipulation of the catheter, increasing the possibility of embolism and blockage of the circulation to vital organs. Inhibitor-coated substances provide similar advantages for artificial or prosthetic heart valves, intra-aortic balloon pumps, total or artificial heart or heart assist devices, intracaval devices, and any device in contact with the bloodstream. In addition, inhibitor-coated devices provide advantages for intracavity devices such as intraperitoneal dialysis catheters and subcutaneous implants where the thrombogenesis-induced inflammatory reactions would be diminished.

Likewise, TABLES 3 and 4 outline exemplary methods of preparing the soluble, pharmacological agent, wherein "SMCC" refers to "succinimidyl, 4-(N-maleimidomethyl)-cyclohexane-1-caroboxylate."

TABLE 3

| STEP # | PROCESS |
|---|---|
| 1) | HSA → Traunt's → HSA—SH |
| 2) | Inhibitor + SMCC → Inhibitor-SMCC |
| 3) | HSA—SH + Inhibitor-SMCC → Inhibitor-SMCC—HSA |

TABLE 4

| STEP # | PROCESS |
|---|---|
| 1) | Inhibitor + Traunt's → Inhibitor-SH |
| 2) | HSA + SMCC → HSA—SMCC |
| 3) | Inhibitor-SH + HSA—SMCC → Inhibitor-SMCC—HSA |

Figures 2, 3:
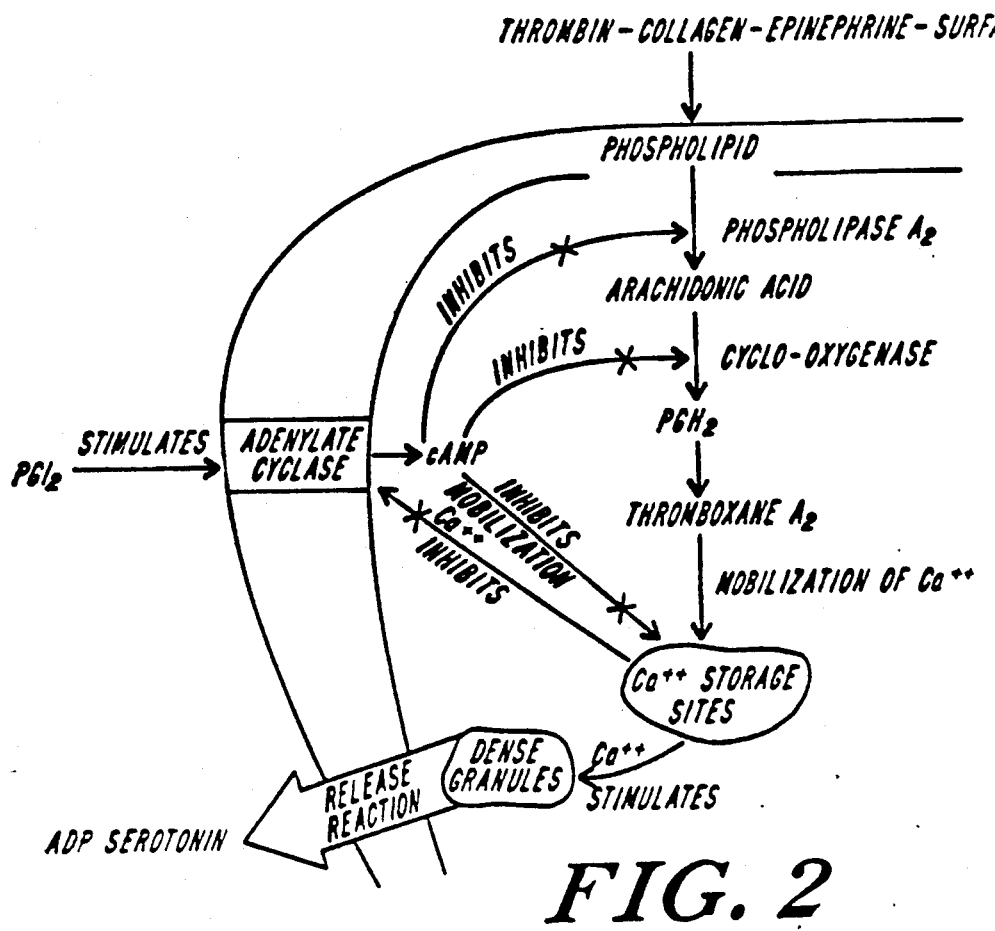
FIG. 2 is a diagrammatic representation of platelet involvement in thrombogenesis.
FIG. 3 is a schematic representation of the amino acid sequence of native hirudin.

Thrombogenesis inhibitors useful for these purposes include hirudin and active analogs, active fragments, active derivatives, and active fusion products thereof, and mixtures thereof. Hirudin is a protein isolated from the saliva of leeches, the amino acid sequence of which is shown in FIG. 3. Hirudin has been shown to reduce platelet adhesiveness, a characteristic which is probably attributed to its mode of action on thrombin. This property alone makes hirudin a most attractive anticoagulant when synthetic surfaces interface with blood. It also selectively inhibits the ability of thrombin to be proteolytic, to be mitogenic for fibroblasts, to activate platelets, and to have chemotatic properties for monocytes and Polymorphonuclear leukocytes. In addition, the immobilized hirudin-thrombin complex may downregulate the events of thrombin mediated chemotaxis. This is a significant event as chronic inflammation may be due to the release by polymorphonuclear leukocytes of degradative enzymes and superoxides throughout the graft that show effects at the sites of the anastomosis, contributing to anastomotic hyperplasia.

A number of synthetic and recombinant hirudin analogs exist (e.g., CGP39393 produced by recombinant DNA techniques by Ciba-Geigy, Basel, Switzerland; PCT W079/00638; PCT W086/03517) which are at least equally useful as thrombogenesis inhibitors.

In addition, active fragments of the native or analog forms of hirudin which have the same biological activities as the whole native or analog forms are also useful. See, e.g. Krstenan Sky et al. (Thrombosis Research (1988) 52:137–141) for a discussion of the activity of C-terminal fragments of hirudin; Wallace et al. (Biochem. (1989) 28:10079–10084) and Chang et al. (FEBS Lett. (1990) 260:209–212) for a discussion of N-terminal fragments of hirudin, among other fragments.

The thrombogenesis inhibitor is directly or indirectly immobilized to the base coat or carrier via the use of a bifunctional cross-linking reagent. In particular, a heterobifunctional cross-linking reagent which has two different reactive groups at each end of a linear molecule, and can therefore bind two different reactive groups on other molecules or on a different region of the same molecule, is most useful as a bifunctional cross-linking agent. For example, photoreactive cross-linkers, such as sulfosuccinimidyl 2-(m-azodo-o-nitro-benzamido)-ethyl-1, 3'-dithio-propionate (SAND), or N-succinimidyl-6-(4-azoido-2'-nitrophenyl-amino) hexanoate (SANPAH) have a photoreactive group that can directly insert into C-H bonds of the base coat by photochemical coupling, while the other group remains free to bind to proteins.

Other useful and preferable cross-linking reagents (such as SPDP and SMCC) and their characteristics are found in TABLE 5. In TABLE 5, the "Double-Agent Number" listed for each reagent is the commercial designation for the reagent as made available by Pierce Chemical Co. (Rockford, Illinois).

TABLE 5

CROSS-LINKING REAGENTS
(part A)

| Double-Agent Number | Double-Agent Acronym | Bifunctionality Homo | Bifunctionality Hetero | Reactive towards: $NH_2$ | Reactive towards: SH | Photo-Reactive |
|---|---|---|---|---|---|---|
| 21551 | ANB-NOS | | X | X | | X |
| 20106 | APB | | X | | X | X |
| 20107 | APG | | X | | | X |
| 21559 | APTP | | X | | X | X |
| 21579 | BS³ | X | | X | | |
| 22319 | BMH | X | | | X | |
| 21554 | BSOCOES | X | | X | | |
| 21524 | DFDNB | X | | X | | |
| 20047 | DIDS | X | | X | | |
| 20664 | DMA | X | | X | | |
| 20666 | DMP | X | | X | | |
| 20668 | DMS | X | | X | | |
| 22585 | DSP | X | | X | | |
| 21555 | DSS | X | | X | | |
| 20590 | DST | X | | X | | |
| 20665 | DTBP | X | | X | | |
| 22590 | DTBPA | X | | | | X |
| 21577 | DTSSP | X | | X | | |
| 21550 | EADB | | X | X | | X |
| 21565 | EGS | X | | X | | |
| 23700 | FNPA | | X | X | | X |
| 21560 | HSAB | | X | X | | X |
| 26095 | MABI | | X | X | | X |
| 22310 | MBS | | X | X | X | |
| 27715 | NHS-ASA | | X | X | | X |
| 20669 | PNP-DTP | | X | X | | X |
| 21552 | SADP | | X | X | | X |
| 21549 | SAND | | X | X | | X |
| 22588 | SANPAH | | X | X | | X |
| 27716 | SASD | | X | X | | X |
| 22325 | SIAB | | X | X | X | X |
| 22320 | SMCC | | X | X | X | |
| 22315 | SMPB | | X | X | X | |
| 21557 | SPDP | | X | X | X | |
| 21556 | Sulfo-BSOCOES | X | | X | | |
| 20591 | Sulfo-DST | X | | X | | |
| 21556 | Sulfo-EGS | X | | X | | |

TABLE 5-continued

CROSS-LINKING REAGENTS

| 22312 | Sulfo-MBS | X | X | X |  |
| 21553 | Sulfo-SADP |  | X | X | X |
| 22589 | Sulfo-SANPAH |  | X | X | X |
| 22327 | Sulfo-SIAB | X | X | X |  |
| 22322 | Sulfo-SMCC | X | X | X |  |
| 22317 | Sulfo-SMPB | X | X | X |  |
| 26101 | TRAUNT'S | X |  | X |  |

| | (part B) |
|---|---|
| Agent Acronym | Chemical Name |
| ANB-NOS | N-5-azido-2-nitrobenzoyloxysuccinimide |
| APB | p-azidophenacyl bromide |
| APG | p-azidophenyl glyoxal |
| APTP | n-4-(azidophenylthio)phthalimide |
| $BS^3$ | bis(sulfosuccinimidyl) suberate |
| BMH | bis maleimidohexane |
| BSOCOES | bis[2-(succinimidooxycarbonyloxy)-ethyl]sulfone |
| DFDNB | 1,5-difluoro-2,4-dinitrobenzene |
| DIDS | 4,4'-diisothiocyano-2,2'-disulfonic acid stilbene |
| DMA | dimethyl adipimidate-2 HCl |
| DMP | dimethyl pimelimidate-2 HCl |
| DMS | dimethyl suberimidate-2 HCl |
| DSP | dithiobis(succinimidylpropionate) |
| DSS | disuccinimidyl suberate |
| DST | disuccinimidyl tartarate |
| DTBP | dimethyl 3,3'-dithiobispropionimidate-2-HCl |
| DTBPA | 4,4'-diothiobisphenylazide |
| DTSSP | 3,3-dithiobis(sulfosuccinimidyl-propionate) |
| EADB | ethyl-4-azidophenyl 1,4-dithio-butyrimidate |
| EGS | ete glycolbis(succinimidyl-succinate) |
| FNPA | 1-azido-4-fluoro-3-nitrobenzene |
| HSAB | N-hydroxysuccinimidyl-4-azidobenzoate |
| MABI | methyl-4-azidobenzoimidate |
| MBS | m-maleimidobenzoyl-N-hydroxysulfo-succinimide ester |
| NHS-ASA | N-hydroxysuccinimidyl-4-azidosalicylic acid |
| PNP-DTP | p-nitrophenyl-2-diazo-3,3,3-trifluoro-propionate |
| SADP | N-succinimidyl(4-axidophenyl)-1,3'-dithiopropionate |
| SAND | sulfosuccinimidyl 2-(m-azido-o-nitro-benzamido)-ethyl-1,3'-dithiopropionate |
| SANPAH | N-succinimidyl-6(4'-azido-2'-nitro-phenyl-amino)hexanoate |
| SASD | sulfosuccinimidyl 2-(p-azidosalicyl-amido)ethyl-1,3'-dithio-propionate |
| SIAB | N-succinimidyl(4-iodoacetyl)amino-benzoate |
| SMCC | succinimidyl 4-(N-maleimidomethyl)-cyclohexane-1-carboxylate |
| SMPB | succinimidyl 4-(p-maleimidophenyl)-butyrate |
| SPDP | N-succinimidyl 3-(2-pyridyldithio) propionate |
| Sulfo-BSOCOES | bis[2-(sulfosuccinimidooxy-carbonyl-oxy)ethyl]sulfone |
| Sulfo-DST | disulfosuccinimidyl tartarate |
| Sulfo-EGS | ethylene glycolbis(sulfosuccinimidyl-succinate) |
| Sulfo-MBS | m-maleimidobenzoyl-N-hydro-xysulfo-succinimide ester |
| Sulfo-SADP | sulfosuccinimidyl(4-azidophenyldithio)-propionate |
| Sulfo-SANPAH | sulfosuccinimidyl 6-(4'azido-2'nithro-phenylamino)hexanoate |
| Sulfo-SIAB | sulfosuccinimidyl(4-iodoacetyl)amino-benzoate |

TABLE 5-continued

CROSS-LINKING REAGENTS

| Sulfo-SMCC | sulfosuccinimidyl 4-(N-maleimido-methyl)cyclohexane-1-carboxylate |
| Sulfo-SMPB | sulfosuccinimidyl 4-(p-maleimido-phenyl)butyrate |
| TRAUNT'S | 2-iminothiolane-HCl |

The cross-linking reagent maybe applied to the base coat in amounts such that the desired binding site density is achieved. Binding site density is that amount of cross-linking reagent, in terms of moles/gram synthetic material, to bind to the base coat while providing confluent coverage of the surface.

To put the inhibitor in condition for linkage to the base coat or carrier, the cross-linking reagent may be initially coupled separately to both the base coat or carrier and to the inhibitor. The kinetic constants of the inhibitors are compared before and after coupling to evaluate effects of the procedure on their kinetic constants. The inhibitor should remain biologically active after being coupled. Therefore, standard activity assays specific for the inhibitor to be immobilized are performed using a standard thrombin solution to evaluate this capacity.

As an alternative, the component of the base coat may be bound to the thrombogenesis inhibitor forming a conjugate prior to its adherence to the synthetic material, and the conjugate bound to the synthetic material as shown in TABLE 2. In addition, thrombogenesis inhibitor conjugate retains biological activity, and can be used as an agent to increase the half life in the circulation as it is not easily cleared by the kidney.

In the special case of SPDP derivatization of hirudin, linkage of certain groups on hirudin to SPDP may destroy hirudin's biological activity because at least some of these groups are required for activity. However, by adjusting the reaction ratio of hirudin to SPDP (1:4, mole:mole), and running the reaction at near physiological pH, SPDP becomes somewhat selective for epsilon amino groups. The result of these conditions favor a 1:1 (mole:mole) conjugation ratio of hirudin to SPDP covalently bound without destroying hirudin's biological activity.

SPDP will react with terminal as well as epsilon amino groups. Since derivatization of a terminal amino group can inactivate a biologically active protein, T-BLOCK (Pierce Chemical Co., Rockford, IL) may be used to block that group during SPDP-derivatization. The T-BLOCK is then removed after derivatization to restore biological activity.

The soluble hirudin conjugate has a number of uses. For example, the soluble hirudin conjugate can be used to anticoagulate blood to obtain plasma for in vitro clinical analysis. Anticoagulation of blood is desirable in patients suffering from venous thrombosis, pulmonary embolism, arterial thrombosis, or in patients undergoing angioplasty or insertion of vascular devices. Plasma anticoagulated with hirudin has the advantages that allow plasma analysis to be performed with calcium present and without the adverse effects of heparin.

In addition, hirudin conjugated to a stable, soluble molecule increases hirudin stability in the bloodstream. For example, 0.1 anti-thrombin units (ATU) of hirudin conjugate standard/ml of blood increases normal thrombin time to 45 seconds. A blood sample containing 0.2 ATU of unconjugated hirudin/ml increases patient thrombin time to 90 seconds. Using this knowledge, the amount of hirudin in a patient's plasma can be calculated to be 0.15 ATU if the patient's thrombin time is determined to be 68 seconds.

Hirudin can be cross-linked to a thrombolytic agent such as tissue plasminogen activator, streptokinase, or other thrombogenesis inhibitors. This inhibitor/agent conjugate has the benefit of maintaining its anticoagulant effect and has potent thrombolytic benefits. The invention makes use of the hirudin-conjugate's potent binding constant for thrombin ($Ki = 1.6 \times 10^{-11}$ M), and that large amounts of thrombin are contained within the matrix of the thrombus. This matrix-bound thrombin attracts the hirudin component of the conjugate and is inhibited. In one example, the streptokinase portion induces thrombolysis and dissolves the thrombi.

The invention will be further understood from the following, non-limiting examples.

EXAMPLE 1

A. Pretreatment and Activation of Polyethylene Terphthalate

Polyethylene terphthalate polyester 52 (DuPont) is sectioned into 1.0 cm lengths. The lubricant on and in the woven surface is removed by washing once for 1 hr with carbon tetrachloride, and twice with 100% $CH_3OH$. The methanol is removed by multiple water washes, followed by one wash in Phosphate buffered saline (PBS), pH 7.4.

The graft material is then subjected to alkaline hydrolysis to increase available COOH groups. The material is treated with 0.5 M NaOH at 50° C. for 1 hr. It is then washed with $H_2O$ repeatedly, and the following steps initiated immediately.

B. Carbodiimide Derivatization of Activated Polyethylene Terphthalate

The activated material is placed into 100.0 ml of 10 mM water-soluble EDC in deionized water, pH 4.6–5.0, for 1 hour at RT with constant stirring. The material is removed and washed in PBS to remove excess unbound EDC.

C. Base Coat Layer Formation

The base coat is applied to the lumen of the polyethylene terphthalate graft material. The derivatized polyethylene terphthalate material is incubated in a 5% HSA solution in PBS at 1 ml/cm² graft material for 24 hr at RT with constant stirring. The graft is removed and washed in PBS to remove nonspecifically bound HSA. Approximately 2 μg protein/mg polyethylene terphthalate is covalently bound.

D. Linkage of SPDP to the Base Coat

The HSA-bound polyethylene terphthalate material is incubated in a 1.0 mM solution of SPDP in PBS, pH 7.4, to bind SPDP to the HSA (100 mM SPDP/cm² base coat). Incubation is terminated after 30–40 min at RT. The graft is washed in PBS to remove nonspecifically bound SPDP.

E. Activation of SPDP on Base Coat and Measurement of Binding Site Density

The SPDP-linked material is dried and weighed to obtain its absolute weight. It is then placed in a 50 mM solution of dithiotreitol (DTT) for 5 min at RT. This reaction releases P-2-T from the bound SPDP, and simultaneously forms free sulfhydryl (SH) groups on the base coat. The released P-2-T is quantitated by absorption spectrophotometry at 343 nm using its extinction coefficient ($E = 8.08 \times 10^3$), and is directly proportional to the quantity of bound SPDP or binding sites. The number of binding sites are calculated and expressed as moles of sites/g of polyethylene terphthalate.

The material is then washed 5 times in PBS and 4 times in $dH_2O$.

F. Linkage of SPDP to Hirudin

Lyophilized hirudin is resuspended in PBS at 1 mg/ml. SPDP (Pharmacia, Piscataway, NJ) is dissolved in 100% ETOH to 10 mM. One part hirudin is mixed with 4 parts SPDP (mole:mole), and incubated for 30 min at RT. SPDP-bound-hirudin is then separated from free SPDP and reaction by-products by chromatography on a G-25 column; the derivatized hirudin is eluted first.

G. Measurement of SPDP Bound to Hirudin

The binding of SPDP to hirudin can be quantitated by the addition of DTT which liberates P-2-T from SPDP bound to hirudin, and which can be measured spectrophotometrically at 343 nm. From this measurement, the moles of SPDP bound to hirudin can be calculated. Each P-2-T released represents one covalent attachment of SPDP to hirudin. One mole of hirudin binds per 1.2 moles SPDP in the present studies.

H. Linkage of Derivatized Hirudin to Base Coat

The reduced SPDP-linked base coat (having free SH groups) is washed with PBS to remove the DTT. SPDP-linked hirudin is then added to the graft at 50.0 μg/cm² polyethylene terphthalate. The solution is incubated overnight at RT to allow the binding of SPDP-hirudin to SH groups on the polyethylene terphthalate graft. The polyethylene terphthalate material with hirudin covalently immobilized thereto is then washed and stored in PBS.

I. Analysis

1. Spectrophotometric Assays:

To quantitate the amount of SPDP-hirudin immobilized on the base coat, an absorbance reading is taken at 343 nm of the solution at the time of the addition of SPDP-hirudin to the polyethylene terphthalate. After the overnight incubation period, another absorbance reading is taken, and the change in absorbance is due to the quantity of P-2-T released from SPDP-hirudin. The amount of P-2-T released is directly proportional to the number of SPDP substitution reactions that have occurred between the base coat SH groups and SPDP-hirudin.

2. Thrombin Inhibition Assay:

Using a known amount of thrombin, a standard curve is constructed with known amount of hirudin or hirudin analog by adding hirudin to thrombin, and measuring residual thrombin activity using chromatographic substrate S-2238. Thrombin inhibition by derivatized hirudin (hirudin-SPDP) or immobilized hirudin (the polyethylene terphthalate material with immobilized hirudin) is then compared to nonderivatized hirudin values by equating ED50 values using 10 NIH units/ml thrombin, and measuring residual thrombin activity.

EXAMPLE 2

A. Derivatization of Hirudin-SMCC 3 mg of hirudin analog (Ciba-Geigy, Basel, Switzerland) is placed into borosilicate glass test tube. 1 ml of a 0.62 mg/ml solution of a $^{125}$I-hirudin is added containing 3 mg of hirudin. A protein concentration of 3.53 mg/ml is determined by Lowry protein assay, and a specific activity of $6.34 \times 10^7$ cpm/mg is calculated via gamma counting. 5 mg of sulfosuccinimidyl 4-(N-maleimidomethyl) cyclohexane 1-carboxylate (Sulfo-SMCC; Pierce Chemical Co., Rockford, IL) is placed into a borosilicate test tube containing 1 ml of Phosphate buffer (0.1 potassium phosphate (dibasic), 0.1 M sodium chloride pH 7.4). The SMCC solution is allowed to stand at room temperature for 15 min with occasional mixing. To obtain a 1:8 (mole:mole) ratio of hirudin to SMCC, 0.36 ml of SMCC is added to 1 ml of the $^{125}$I-hirudin mixture while the hirudin mixture is stirring. The hirudin-SMCC mixture is allowed to incubate at room temperature for 30 min, with occasional mixing. During the incubation period, a Pharmacia PD-10 Sephadex Column (Pharmacia, Piscataway, NJ), is equilibrated with phosphate buffer. This column is then used to separate the hirudin-SMCC from free SMCC after the one hour incubation period. The hirudin-SMCC mixture is then placed into an orbital shaker (water bath temperature = 37° C.) for 30 min with occasional stirring. The remaining phosphate buffer in the column is drained off and the hirudin-SMCC mixture added to the column. The mixture is then eluted with phosphate buffer. Fractions are collected in borosilicate test tubes, and the absorbance of each fraction is read at 280 nm using a Beckman DU-64 Spectrophotometer (Beckman, Fullerton, CA). The first peak fractions (hirudin-SMCC) are pooled and the absorbance at 280 nm read. The protein concentration in the pooled fraction is determined to be 1.47 +/− 0.18 mg/ml (n=2) using the extinction coefficient for hirudin (4.25) and the gamma counts.

B. Derivatization of Sulfhydryl Bovine Serum Albumin 20 mg of bovine serum albumin (BSA, Sigma Chemical Co., St. Louis, MO) is placed into a borosilicate test tube which contained 1 ml of phosphate buffer. 9 mg of 2-Iminothiolane-HCl (Traunt's Reagent; Pierce Chemical Co., Rockford, IL) is placed into a borosilicate test tube containing 1 ml of phosphate buffer. To obtain a 1:20 (mole:mole) ratio of BSA to Traunt's, 0.1 ml of the Traunt's solution is added to the BSA solution while the BSA was mixing. The BSA-Traunt's solution is allowed to incubate at room temperature for 30 min. During the incubation period, a PD-10 Sephadex column (Pharmacia, Piscataway, NJ) is equilibrated using the same equilibration described above. The BSA-Traunt's solution is then transferred to the orbital shaker (water bath temperature = 37° C.) for 30 min and mixed occasionally. The remaining phosphate buffer in the PD-10 column is drained off and the BSA-Traunt's solution added to the column. The solution is then eluted with phosphate buffer. Twelve-1 ml fractions are collected in borosilicate test tubes. The absorbance of each fraction is read at 280 nm using a spectrophotometer. The first three peak fractions (BSA-SH) are pooled and the absorbance at 280 nm read. Using the extinction coefficient of BSA, 9.6 mg/ml of BSA-SH is calculated to be present in the pooled BSA-SH fraction.

C. Derivatization of BSA-SMCC-Hirudin Conjugate

To bind the BSA-SH to the hirudin-SMCC, an 1:1 (mole:mole) ratio is used. 1.5 ml of BSA-SH is added to 1.5 ml of the hirudin-SMCC solution. The solution is mixed and then allowed to stand overnight at room temperature.

D. Purification of the BSA-SMCC-Hirudin Conjugate

In order to separate the conjugate from other impurities (i.e. unbound hirudin-SMCC, free SMCC, and BSA aggregates), HPLC was performed using a Shimadzu (Braintree, MA) LC6A High Performance Liquid Chromatograph (HPLC) connected to a Pharmacia (Piscataway, NJ) Superose 12 column. The column is equilibrated with HPLC grade phosphate buffer (0.1 M phosphate buffer, 0.1 M sodium chloride pH 7.4) at a flow rate of 0.4 ml/min for 1.5 hours. After equilibration, a 1 ml low molecular weight tri-standard solution consisting of 1.5 mg/ml Aldolase (mol. wt. = 150 kD), 6.0 mg/ml BSA (mol. wt. = 67 kD), and 1.5 mg/ml Ribonuclease A (mol. wt. = 13 kD) (Pharmacia, Piscataway, NJ) is prepared.

Figure 4A:
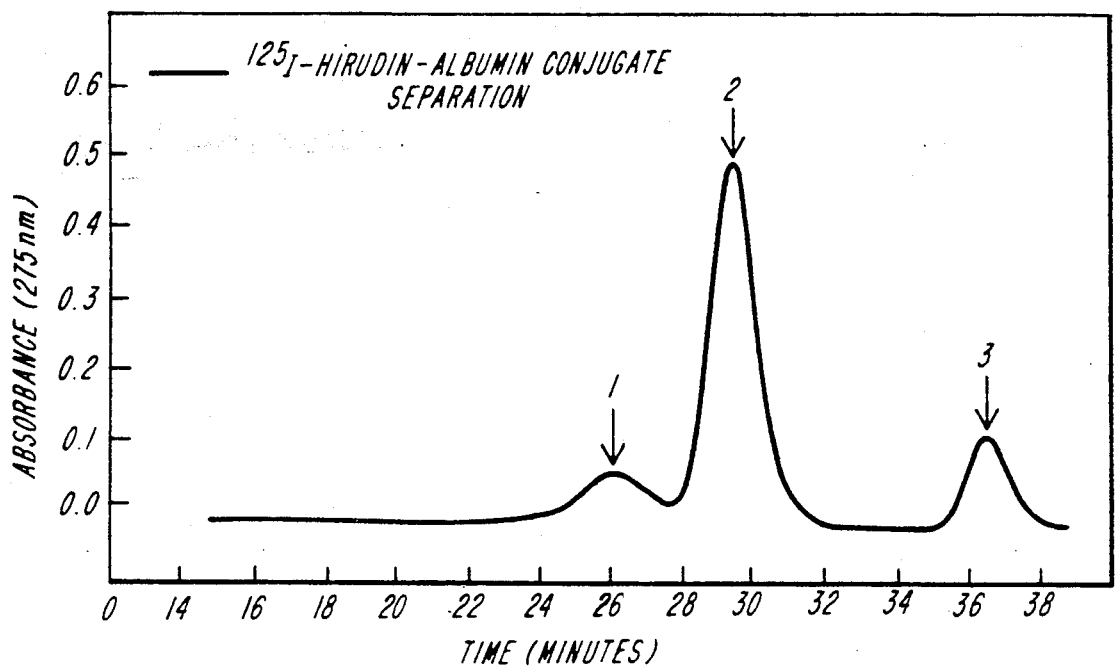
FIGS. 4A—4C are schematic representations of optical scans of HPLC-separated hirudin-albumin conjugates.
Figure 4B:
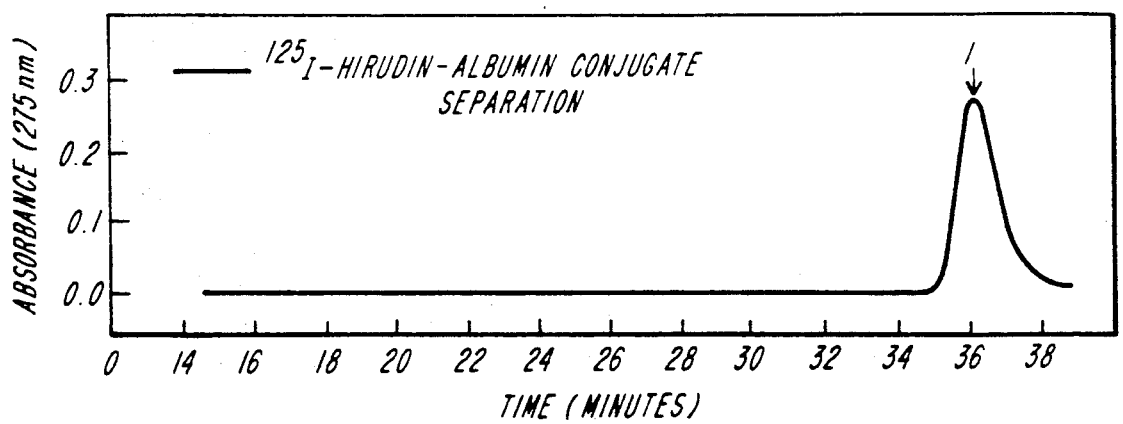
Figure 4C:
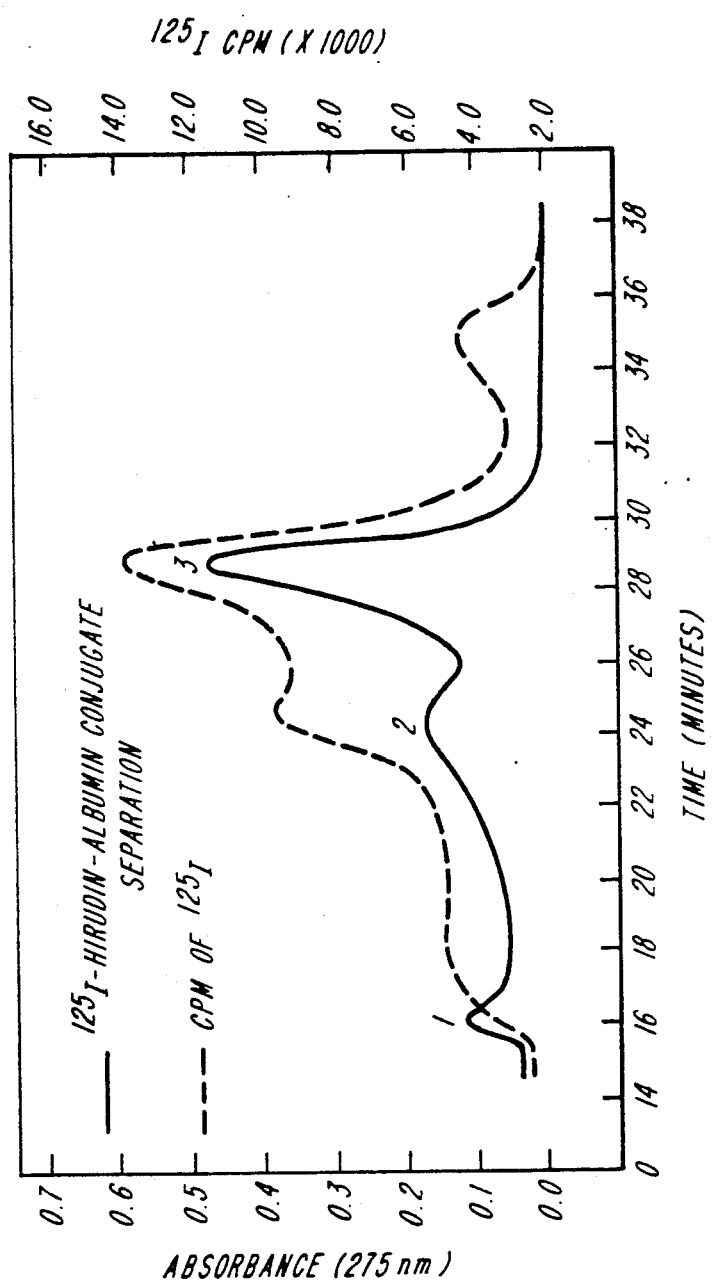

FIG. 4C shows the purification of the conjugate by HPLC in comparison to low molecular weight standards (FIG. 4A, peak 1 is 150 kD, peak 2 is 67 kD, and peak 3 is 13 kD) and to purified recombinant hirudin standard (FIG. 4B, peak 1 is 6965 D). The material isolated from peaks 1, 2 and 3 in FIG. 4C have molecular weights of 300 kD, 160 kD, and 70 kD. Isolates of peak 1 and 2 material appear to be aggregates of albumin conjugates, whereas peak 3 material forms albumin:hirudin conjugates at a mole-to-mole ratio of 1:5. Aggregates similar to those in the material in peaks 1 and 2 cannot form on Prosthetic surfaces, as the derivatized hirudin is linked to the albumin carrier previously bound to the surface.

Figure 5A:
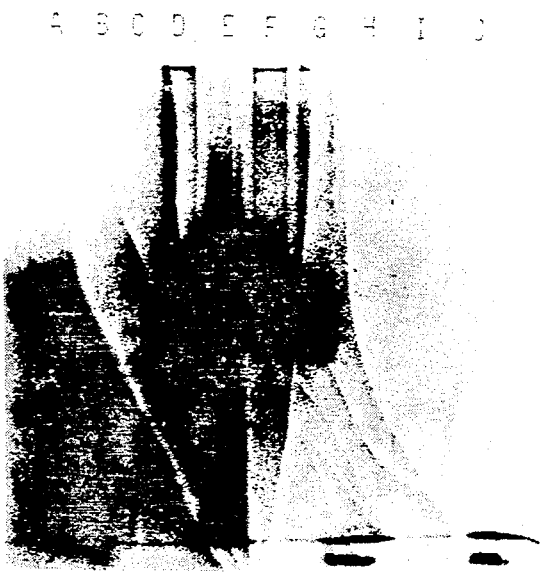
FIG. 5 is a photographic representation of (A) an SDS-polyacrylamide gel and (B) autoradiogram of the soluble hirudin-albumin conjugate agent that had been HPLC purified and separated.
Figure 5B:

Confirmation of HPLC separation can be demonstrated by PAGE and autoradiography as shown in FIG. 5A and FIG. 5B, respectively. In the gel shown in FIG. 5A, lane A is HPLC peak 3 (see FIG. 4C) used for kinetic studies; lane B is HPLC Peak 2 (see FIG. 4C) approx. 200 kD conjugate aggregate; lane C is HPLC peak 1 (see FIG. 4C) approximately 1 kD aggregates of mostly albumin with trace amounts of hirudin; lane D is a $^{125}$I-hirudin and albumin conjugation mixture before HPLC separation; lane E is molecular weight standards (top to bottom): 96 kD, 68 kD, 36 kD, and 29 kD; lane F is a $^{125}$I-hirudin and albumin conjugation mixture before HPLC separation; lane G is bovine serum albumin; lane H is low molecular weight standards; lane I is 125I-hirudin; and lane J is low molecular weight standards. These separation analyses demonstrate excellent conjugation stability, as free hirudin is not detected by either means of analysis.

These results demonstrate that the hirudin-albumin conjugate inhibits thrombin-mediated platelet aggregation and release, an important finding when considering platelet surface-mediated events and the ability of thrombin to adsorb to surfaces.

The inhibiting potency of thrombin platelet aggregation by hirudin and the conjugate compare to the kinetic study results in section B. below. These studies show that hirudin covalently linked to albumin with a heterobifunctional cross-linker 1) is stable and durable in vitro: 2) binds thrombin potently and reversibly; 3) loses insignificant activity to inhibit thrombin enzymatic activity; and 4) loses insignificant activity to inhibit thrombin stimulated platelet aggregation.

E. Kinetic Evaluation of the Hirudin-Albumin Conjugate

Peak 3 conjugate material (shown in FIG. 4C and lane A in FIG. 5A) is evaluated by kinetic analysis. Kinetic evaluation of the ability of the peak 3 conjugate to inhibit thrombin activity is compared to hirudin alone. Hirudin is observed to be a noncompetitive inhibitor of a linear mixed type. The conjugate is found to be a pure, noncompetitive inhibitor. These determinations are made by Lineweaver-Burke and Dixon plot analyses. The inhibitor constant for hirudin is determined to be $1.7 \times 10^{-12}$. The inhibitor constant for the conjugate is $1.8 \times 10^{-11}$. There is a 10-fold loss in binding affinity when comparing the Ki values of hirudin to the conjugate, respectively. In a biologic or physiologic system, the different abilities of hirudin and conjugate to inhibit thrombin are insignificant.

F. Inhibition of Thrombin-Mediated Platelet Aggregation

Investigation of the biologic activity of hirudin covalently linked to albumin is examined by inhibiting thrombin-mediated platelet aggregation. A whole blood platelet aggregometer (Chronolog Corp., Havertown, PA) is used to measure platelet aggregation and simultaneous ATP release. Platelet aggregation is selected to quantify inhibition of thrombin events other than fibrin formation. The results are shown in TABLE 6.

TABLE 6

| Thrombin NIHU[1] | Inh. ATU[2] | Aggreg. OHMS/6 min. | % Inh. Plate. Aggreg. | ATP Release | % Inh. ATP Release |
|---|---|---|---|---|---|
| 0.1 | — | 32.9 | 0 | 1.36 μM | 0 |
| 0.1 | H[3]1.15 | 0 | 100 | 0 | 100 |
| 0.1 | H 0.12 | 15.7 | 52 | 0.60 | 56 |
| 0.1 | C[4]1.46 | 0 | 100 | 0 | 100 |
| 0.1 | C 0.73 | 0 | 100 | 0.24 | 82 |
| 0.1 | C 0.55 | 26.6 | 20 | 1.08 | 21 |
| 0.1 | C 0.30 | 29.6 | 10 | 1.17 | 14 |

[1] a standardized unit of enzymatic activity
[2] anti-thrombin unit or that amount of inhibitor which inhibits the enzymatic activity of 1 NIH unit of thrombin
[3] hirudin
[4] hirudin-albumin conjugate These results demonstrate that thrombin-stimulated platelet aggregation is inhibited by both hirudin alone and by the $^{125}$I-hirudin-albumin conjugate. Similarly, ATP release is also inhibited. By calculation (using hirudin results at 0.12 ATU and conjugate at 0.55 ATU) the conjugate loses 10-fold the inhibitory capacity when compared to hirudin alone. This is a minor loss as the conjugated hirudin still inhibits thrombin greater than anti-thrombin III, a natural thrombin inhibitor, by approximately 10,000 fold.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. A soluble, biocompatible, pharmacological agent for inhibiting thrombin generation and thrombus formation comprising:
   (a) a soluble, biocompatible carrier "selected from the group consisting of a protein, peptide, lipoprotein, glycoprotein, glycosaminoglycan and mixtures thereof"; and
   (b) a thrombogenesis inhibitor covalently immobilized on said carrier, said inhibitor being hirudin or an active analog or active fragment thereof.

2. The agent of claim 1 wherein said comprises a protein.

3. The agent of claim 2 wherein said protein is selected from the group consisting of serum albumin, fibronectin, and mixtures thereof.

4. The agent of claim 3 wherein said protein comprises serum albumin.

5. The agent of claim 3 wherein said protein comprises fibronectin.

6. The agent of claim 1 further comprising a bifunctional cross-linking reagent linking said thrombogenesis inhibitor to said carrier.

7. The agent of claim 6 wherein said bifunctional cross-linking reagent comprises a heterobifunctional cross-linking reagent.

8. The agent of said claim 6 wherein said heterobifunctional cross-linking reagent comprises 3-(2-pyridyldithio)propionate.

9. The agent of claim 6 wherein said bifunctional cross-linking reagent comprises a homobifunctional cross-linking reagent.

10. A method of producing a soluble, biocompatible, pharmacological agent useful for inhibiting thrombin generation and thrombus formation, said method comprising the step of convalently immobilizing a thrombogenesis inhibitor on a soluble, biocompatible carrier selected from the group consisting of a protein, peptide, lipoprotein, glycoprotein, glycosaminoglycan and mixtures thereof, said inhibitor being hirudin or an active analog or active fragment thereof, and said carrier binding said thrombogenesis inhibitor.

11. The method of claim 10 wherein said immobilizing step comprises the steps of:
   (a) contacting said thrombogenesis inhibitor with at least one molecule of a bifunctional cross-linking reagent for a time sufficient to allow linkage of said reagent to said thrombogenesis inhibitor; and
   (b) binding said thrombogenesis inhibitor-linked reagent to said carrier.

12. The method of claim 10 wherein said contacting step comprises:
   (a) contacting said carrier with at least one molecule of a bifunctional cross-linking reagent for a time sufficient to allow linkage of said reagent to said carrier; and
   (b) binding said carrier-linked reagent to said thrombogenesis inhibitor.

13. The method of claim 12 wherein said contacting step further comprising contacting said thrombogenesis inhibitor with at least one molecule of said bifunctional cross-linking reagent for a time sufficient to allow linkage thereto,
   and said binding step further comprises binding said carrier-linked reagent to said thrombogenesis inhibitor-linked reagent.

14. The method of claim 11 wherein said contacting step comprises contacting said thrombogenesis inhibitor with a bifunctional cross-linking reagent selected from the group consisting of heterobifunctional cross-linking reagents, homobifuntional cross-linking reagents, and mixtures thereof.

15. The method of claim 12 wherein said contacting step includes contacting said carrier with a bifunctional cross-linking reagent selected from the group consisting of heterofunctional cross-linking reagents, homobifuntional cross-linking reagents, and mixtures thereof.

16. The method of claim 14 wherein said contacting step includes contacting said thrombogenesis inhibitor with the heterobifunctional cross-linking reagent, 3-(2-pyridyldithio)propionate.

17. The method of claim 15 wherein said contacting step includes contact thrombogenesis inhibitor with the heterobifunctional cross-linking reagent, 3-(2-pyridyldithio)propionate.

18. The method of claim 11 further comprising the steps of:
(a) reducing said carrier to expose a sulfhydryl group thereon;
(b) contacting said exposed sulfhydryl group with said inhibitor-linked reagent; and
(c) inducing a substitution reaction between said sulfhydryl group and said inhibitor-linked reagent,
said reaction resulting in linkage of said carrier to said inhibitor.

* * * * *